US00PP33249P3

(12) United States Plant Patent
Mercuri et al.

(10) Patent No.: US PP33,249 P3
(45) Date of Patent: Jul. 13, 2021

(54) ORANGE TREE NAME 'VILLA11'

(50) Latin Name: *Citrus sinensis*
Varietal Denomination: Villa11

(71) Applicants: Frank Mercuri, Leeton (AU); Domenic Mercuri, Leeton (AU); Frank Nardi, Leeton (AU); Michael Nardi, Leeton (AU); Joe Nardi, Leeton (AU)

(72) Inventors: Frank Mercuri, Leeton (AU); Domenic Mercuri, Leeton (AU); Frank Nardi, Leeton (AU); Michael Nardi, Leeton (AU); Joe Nardi, Leeton (AU)

( * ) Notice: Subject to any disclaimer, the term of this patent is extended or adjusted under 35 U.S.C. 154(b) by 0 days.

(21) Appl. No.: 16/974,058

(22) Filed: Sep. 16, 2020

(65) Prior Publication Data

US 2021/0105921 P1 Apr. 8, 2021

Related U.S. Application Data

(60) Provisional application No. 62/973,474, filed on Oct. 4, 2019.

(51) Int. Cl.
*A01H 5/08* (2018.01)
*A01H 6/78* (2018.01)

(52) U.S. Cl.
USPC ..... Plt./202
CPC ..... *A01H 6/785* (2018.05)

(58) Field of Classification Search
USPC ..... Plt./156, 201, 202
See application file for complete search history.

(56) References Cited

U.S. PATENT DOCUMENTS

PP21,568 P2 * 12/2010 Morgan ..... A01H 6/78
Plt./202

OTHER PUBLICATIONS

G. Sanderson, D. Monks, T. Witte and A. Creek NSW DPI & K. Lacy Dept. Primary Industries and Regional Development, WA (Oct. 19, 2017, Loxton), https://www.dpi.nsw.gov.au/_data/assets/pdf_file/0007/752263/New-variety-highlights-Sanderson-Citrus-roadshow-2017.pdf. (Year: 2017).*

* cited by examiner

*Primary Examiner* — Susan McCormick Ewoldt
*Assistant Examiner* — Karen M Redden
(74) *Attorney, Agent, or Firm* — Michelle Bos Legal LLC

(57) ABSTRACT

A new orange tree named 'Villa11' characterized by its late-maturing fruit.

7 Drawing Sheets

Latin name: *Citrus sinensis.*
Common name: Navel Orange.
Variety denomination: 'Villa11'.

BACKGROUND AND SUMMARY OF THE VARIETY

'Villa11' is a new orange tree, originally discovered in a cultivated orchard near Leeton, New South Wales, Australia in 2015. It is believed to be a spontaneous whole tree mutation of the 'Cara Cara' orange variety (not patented). The 'Villa11' tree was first noticed because its fruit was greener than the fruit on surrounding 'Cara Cara' trees. Upon continued observation, the fruit was found to mature at least two months later than 'Cara Cara'. The new variety was asexually propagated by grafting in 2015 at Leeton, and has since been found to remain true to type over successive asexually propagated generations.

'Villa11' is distinguishable from similar varieties 'Cara Cara' and 'Kirkwood Red' (U.S. Plant Pat. No. 24,778) by its late fruit maturity.

BRIEF DESCRIPTION OF THE PHOTOGRAPHS

The accompanying photographs were taken in 2019 at Leeton, NSW, Australia. The trees depicted were planted in 2015. The colors of the claimed variety may vary with lighting conditions. Color characteristics of the variety should therefore be determined with reference to the observations described herein, rather than from these illustrations alone.

DETAILED BOTANICAL DESCRIPTION

Figure 1:
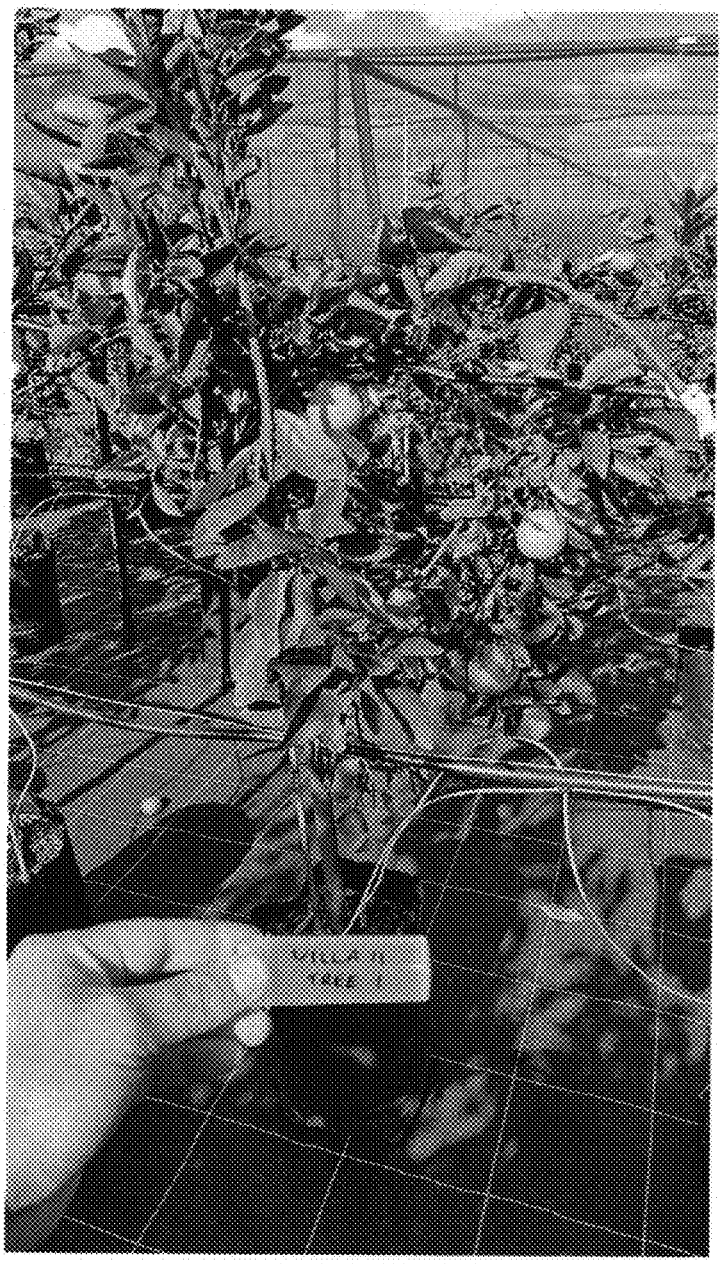
FIG. 1 shows a 'Villa11' orange tree.
Figure 2:
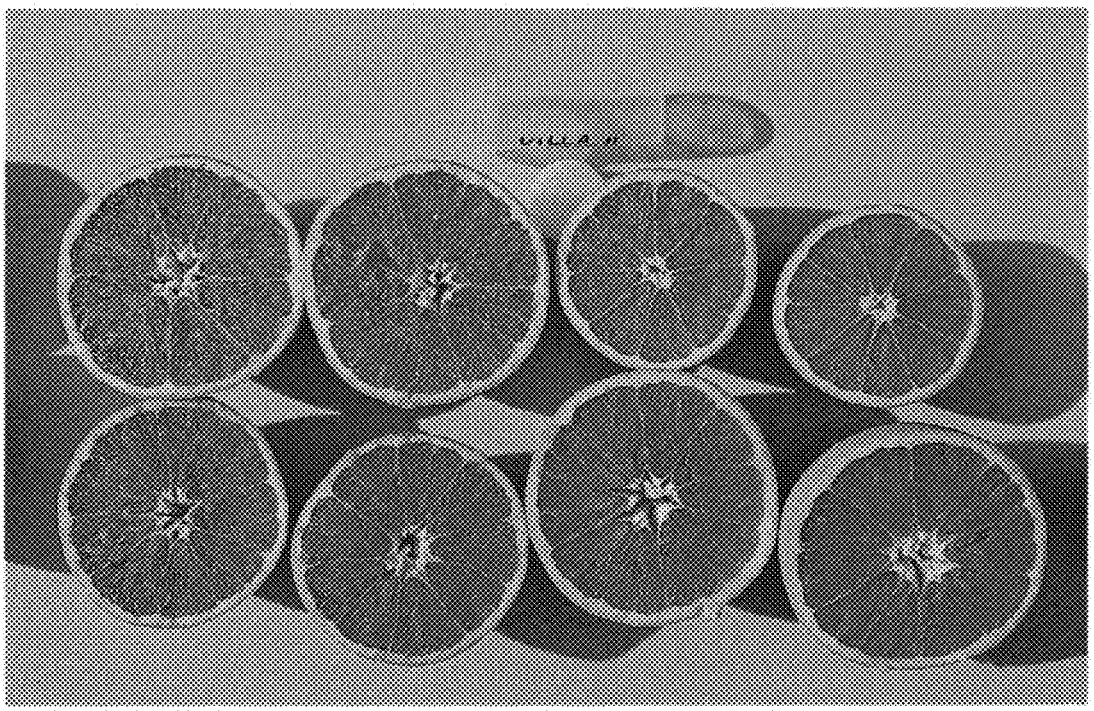
FIG. 2 shows sectioned 'Villa11' oranges.
Figure 3:
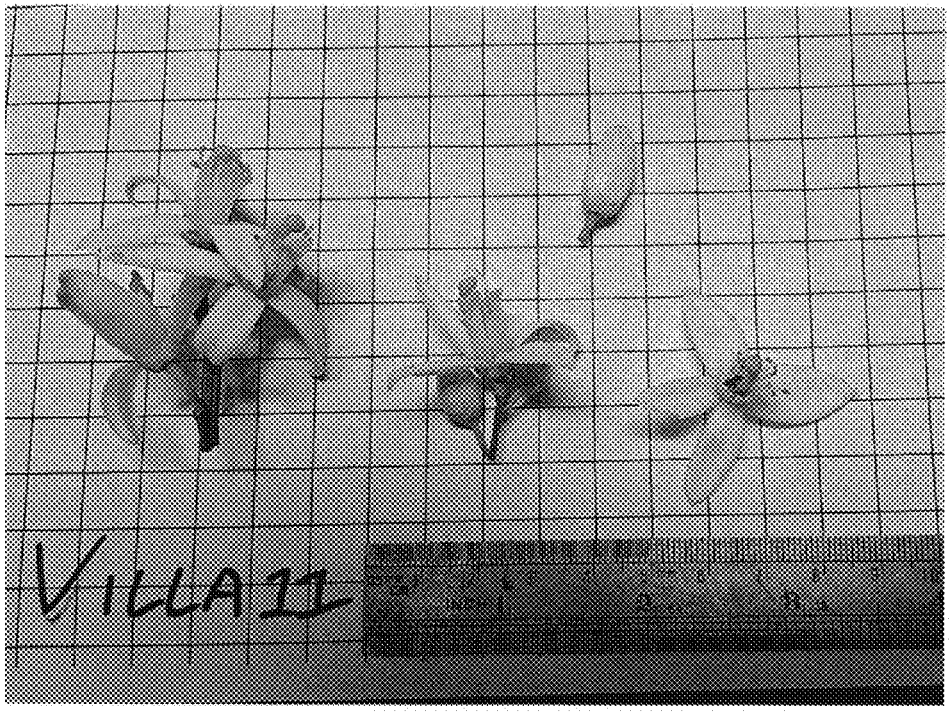
FIG. 3 shows buds and blossoms from a 'Villa11' orange tree.
Figure 4:
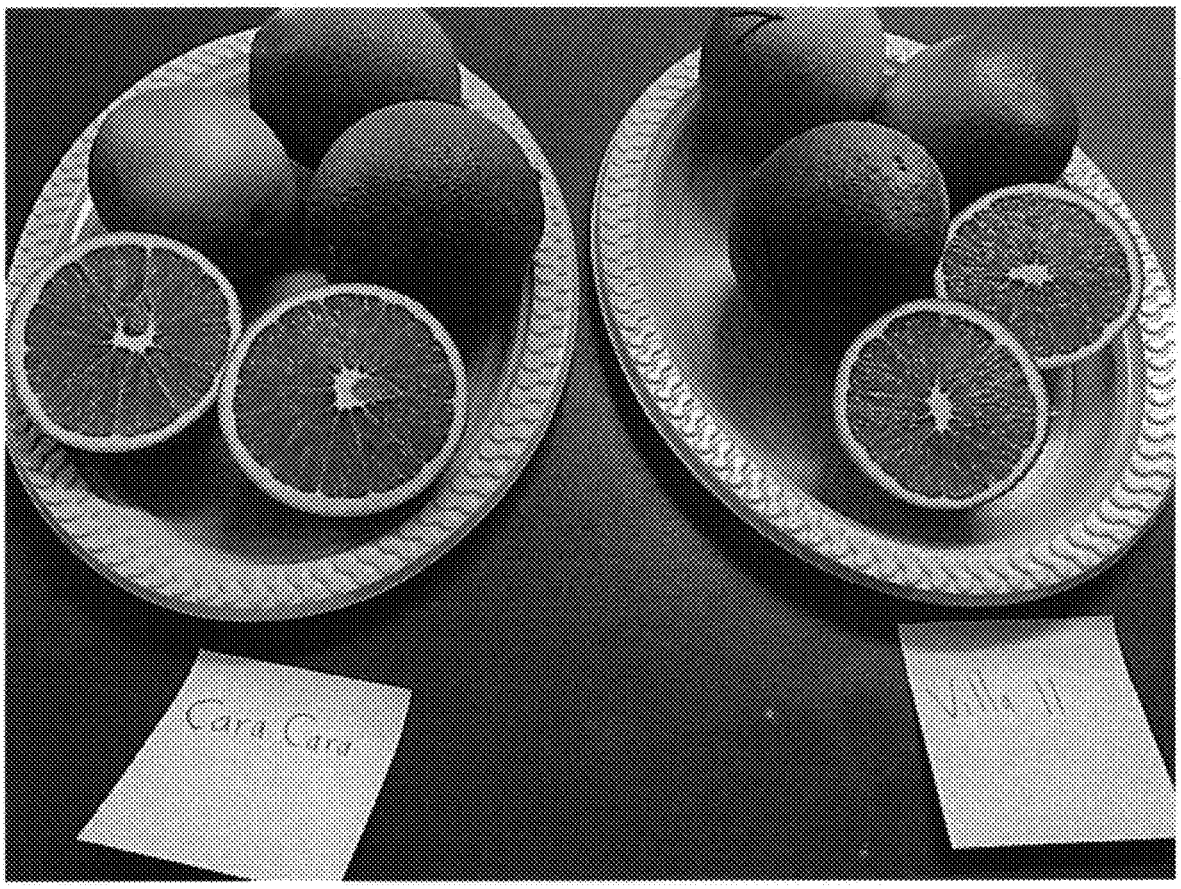
FIG. 4 shows whole and sectioned 'Cara Cara' oranges (left) and 'Villa11' oranges (right)
Figure 5:
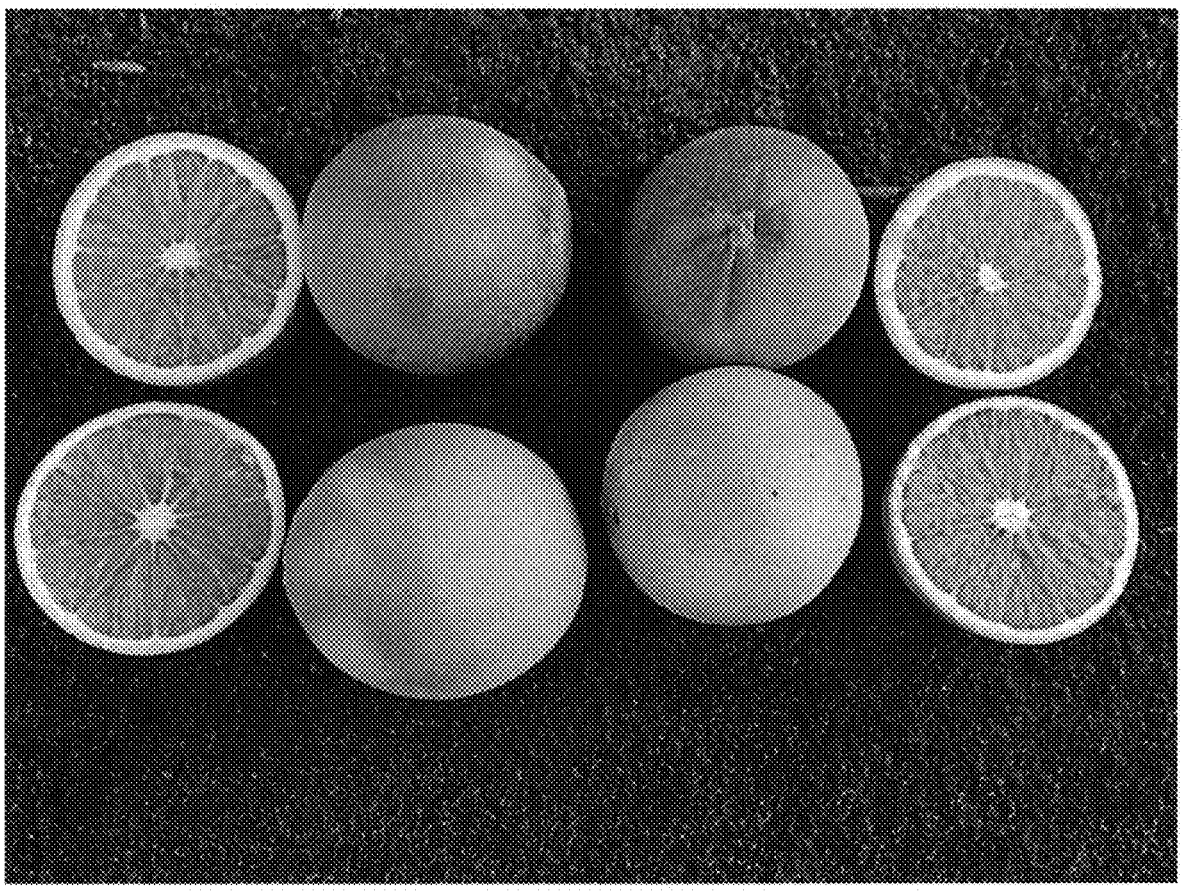
FIG. 5 shows whole and sectioned 'Villa11' oranges (top) and 'Cara Cara' oranges (bottom)
Figure 6:
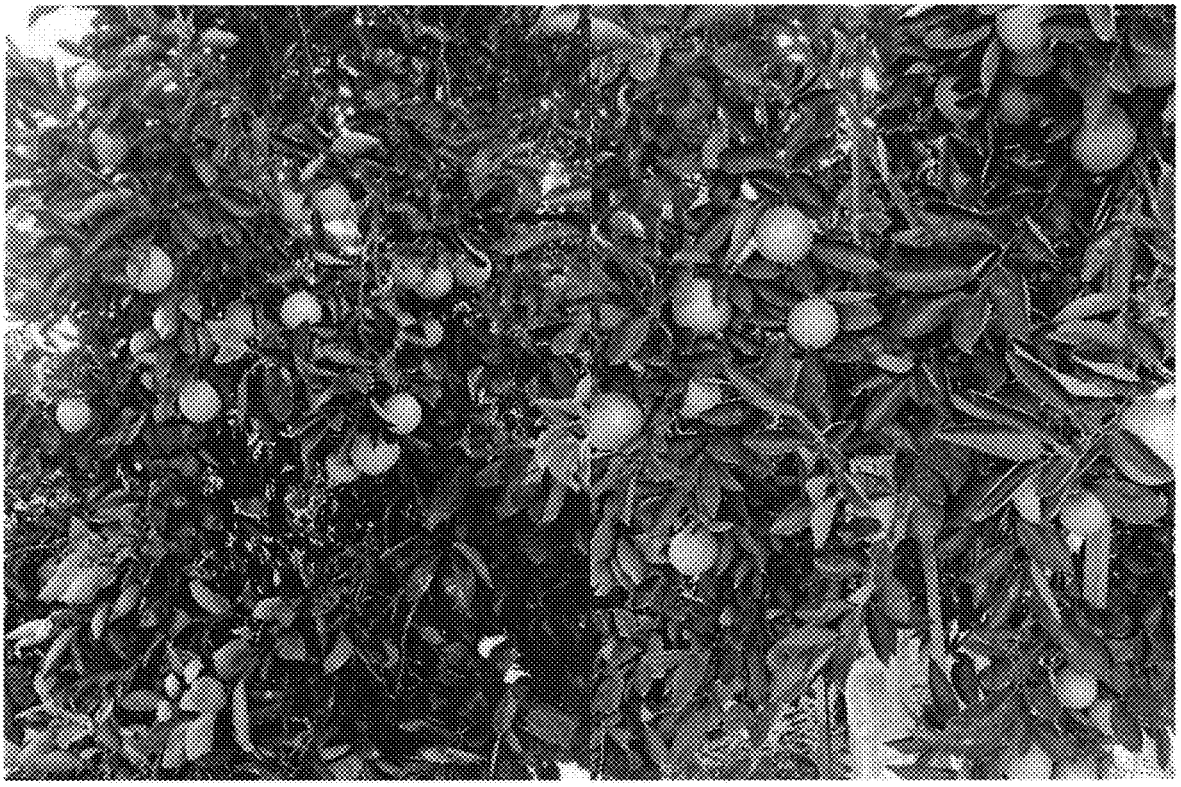
FIG. 6 shows photos taken the same day of a 'Cara Cara' orange tree (left) and a 'Villa11' orange tree (right)
Figure 7:
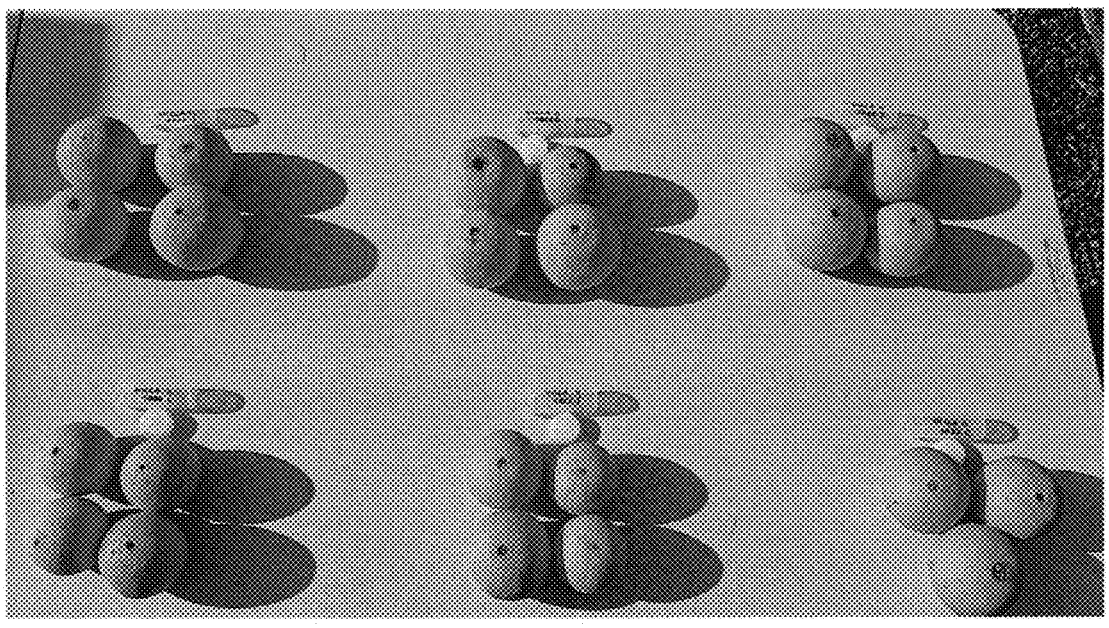
FIG. 7 shows whole 'Villa11' oranges.

The following detailed botanical description is based on observations recorded at Leeton, NSW, Australia from 2015 to 2020. The trees described were planted in 2015 on 'Troyer Citrange' rootstock (not patented). The characteristics described will vary somewhat depending upon cultural practices and climatic conditions, and can vary with location and season. Quantified measurements are expressed as an average of measurements taken from a number of individual plants of the claimed variety. The measurements of any individual plant or any group of plants of the variety may vary from the stated average. Colors are described with reference to The Royal Horticultural Society Colour Chart (6th Ed.).

DETAILED BOTANICAL DESCRIPTION

Tree:

*Vigor*.—Medium, similar to 'Cara Cara'.
*Density of canopy*.—Dense.
*Habit*.—Drooping.
*Height*.—1.5 m to 2 m.
*Spread*.—1.5 m to 2 m.
*Trunk diameter* (*at* 30 *cm above the graft*).—24 mm.
*Bark texture*.—Smooth to medium.
*Bark color*.—Grey-brown N199D.
*Lenticel color*.—Grey-brown N199C.
*Tendency toward alternate bearing*.—Absent.
*Winter hardiness*.—Intermediate.
*Chilling requirement*.—Absent.
*Drought tolerance*.—Intermediate.

Branch:

*Length*.—30 cm.
*Diameter*.—15 mm.
*Crotch angle*.—>45 degrees.
*Bark color*.—Grey-brown N199D.
*Bark texture*.—Smooth.
*Thorns*.—Absent or sparse.
*Thorn length*.—Very short, 5 mm.
*Current year shoot length*.—13.5 cm.
*Current year shoot color*.—Yellow-green 152C.

Flowers:

*Bud shape*.—Elongated.
*Bud length*.—2 cm.
*Bud diameter*.—1 cm.
*Bud color*.—Greenish white 157D.
*Quantity of blossoms per cluster*.—3.
*Relative position of petal margins*.—Not touching.
*Blossom diameter*.—Medium, about 4 cm.
*Pollen*.—Absent.
*Sepal length*.—5 mm.
*Sepal width*.—4 mm.
*Sepal shape*.—Acuminate.
*Sepal margin*.—Entire.
*Sepal color—upper surface*.—Yellow 8A.
*Sepal color—lover surface*.—Yellow 8A.
*Quantity of petals per flower*.—4.
*Petal shape*.—Elliptic.
*Petal apex*.—Acute.
*Petal margin*.—Smooth.
*Petal length*.—Long, 2 cm.
*Petal width*.—Medium, about 1 cm.
*Petal surface texture*.—Smooth.
*Petal color—upper surface*.—White N155D.
*Petal color—lower surface*.—White N155D.
*Date of first bloom*.—September 14.
*Date of full bloom*.—September 17.
*Pedicel length*.—4 mm to 6 mm.
*Pedicel diameter*.—1 mm to 2 mm.
*Pedicel color*.—RHS 149C.
*Pistil quantity per flower*.—1.
*Pistil length*.—Short.
*Pistil color*.—Yellow-green 149C.
*Stigma length*.—1.5 mm to 2 mm.
*Stigma color*.—Yellow-green 150D.
*Style length*.—8 mm to 9 mm.
*Style color*.—Yellow-green 150C.
*Ovary length*.—Short.
*Ovary diameter*.—Broad.
*Ovary color*.—Yellow-green 150A.
*Anther quantity per flower*.—18.
*Anther length*.—1 cm to 1.5 cm.
*Anther color*.—RHS 150D.

Leaves:

*Length*.—Medium to long, 100 mm.
*Width*.—Medium to broad, 62 mm.
*Length/width ratio*.—Approximately 2:1.
*Blade margin*.—Entire.
*Leaf shape*.—Elliptic.
*Apex shape*.—Acute.
*Base shape*.—Cuneate.
*Color of upper surface*.—Yellow-green 152B.
*Color of lower surface*.—Yellow-green 153A.
*Petiole length*.—Medium, 22 mm.
*Wings*.—Present.
*Wing width*.—Medium to broad, 10 mm.

Fruit:

*Axial diameter*.—Short to medium, 94 mm.
*Apical diameter*.—Short to medium, 88 mm.
*Ratio of apical/axial diameter*.—0.94.
*Weight*.—305 g.
*General shape in profile*.—Slightly rounded.
*Position of maximum diameter*.—At middle.
*Depression at distal end*.—Absent.
*Navel*.—Present.
*Areola*.—Absent.
*Rind color*.—Yellow-orange 17A.
*Oil gland diameter*.—Small to medium.
*Oil gland density*.—25 per $cm^2$.
*Rind thickness*.—Medium, 6 mm.
*Ease of peeling*.—Medium.
*Rind texture*.—Smooth to medium.
*Albedo thickness*.—3 mm to 4 mm.
*Albedo color*.—Yellow-white 158C.
*Quantity of fruit segments per fruit*.—10.
*Toughness of segment membrane*.—Medium.
*Juice sac length*.—10 mm.
*Juice sac shape*.—Elongated.
*Juice sac color*.—Orange-red 33A.
*Flesh color*.—Orange-red N32C.
*Juice soluble solids*.—11.45° Brix.
*Relative harvest maturity*.—Late.
*Harvest begins*.—August.
*Seeds*.—Absent.
*Parthenocarpy*.—Present.
*Market use*.—Fresh market.
*Keeping quality*.—Good.
*Shipping quality*.—Good.

We claim:

1. A new and distinct variety of orange tree substantially as described and illustrated herein.

* * * * *